United States Patent [19]
Gore et al.

[11] Patent Number: 5,662,622
[45] Date of Patent: Sep. 2, 1997

[54] INTRAVASCULAR CATHETER

[75] Inventors: Susana M. Gore, Fort Lauderdale; Mark Mueller, Miramar, both of Fla.; Nicholas Green, Kinnelon, N.J.; Jeffrey G. Gold, Parkland, Fla.; Peter P. Soltesz, San Jose, Calif.

[73] Assignee: Cordis Corporation, Miami Lakes, Fla.

[21] Appl. No.: 409,973

[22] Filed: Apr. 4, 1995

[51] Int. Cl.⁶ .................................................. A61M 25/00
[52] U.S. Cl. ........................ 604/282; 604/265; 604/280; 138/123
[58] Field of Search ............................. 604/280, 281, 604/282, 264, 265; 138/123, 124, 125, 140, 130; 427/2.1

[56] References Cited

U.S. PATENT DOCUMENTS

| | | |
|---|---|---|
| 2,437,542 | 3/1948 | Krippendorf . |
| 2,472,483 | 6/1949 | Krippendorf . |
| 3,416,531 | 12/1968 | Edwards . |
| 4,044,765 | 8/1977 | Kline . |
| 4,100,309 | 7/1978 | Micklus et al. .......... 427/2.1 |
| 4,516,972 | 5/1985 | Samson . |
| 4,577,543 | 3/1986 | Wilson . |
| 4,665,604 | 5/1987 | Dubowik . |
| 4,690,175 | 9/1987 | Ouchi et al. .......... 604/282 |
| 4,706,670 | 11/1987 | Andersen et al. . |
| 4,739,768 | 4/1988 | Engelson . |
| 4,817,613 | 4/1989 | Jaraczewski et al. . |
| 4,830,059 | 5/1989 | Silberstang . |
| 4,899,787 | 2/1990 | Ouchi et al. .......... 604/282 |
| 4,955,862 | 9/1990 | Sepetka . |
| 5,037,404 | 8/1991 | Gold et al. . |
| 5,279,596 | 1/1994 | Castaneda et al. . |
| 5,334,169 | 8/1994 | Brown et al. .......... 604/282 |
| 5,358,493 | 10/1994 | Schweich, Jr. et al. . |
| 5,423,773 | 6/1995 | Jimenez .......... 604/282 |
| 5,437,673 | 8/1995 | Baust et al. .......... 604/30 |
| 5,531,715 | 7/1996 | Engelson et al. .......... 604/265 |
| B1 4,739,768 | 11/1994 | Engelson . |

*Primary Examiner*—Corrine M. McDermott
*Assistant Examiner*—Ronald K. Stright, Jr.
*Attorney, Agent, or Firm*—Gerstman, Ellis & McMillin, Ltd.

[57] ABSTRACT

An intravascular catheter carries a helical reinforcement member embedded within at least a portion of the tubular wall of the catheter. The helical reinforcement member comprises a helical first portion having coils of greater pitch than the pitch of helical coils of a second portion. Preferably, the catheter is for insertion into brain arteries, and comprises a flexible tube having an outer diameter of no more that about 0.05 inch, for example 3 French or smaller. The flexible tube defines outer and inner tubular layers. The inner tubular layer surrounds a catheter lumen and comprises a chemically inert fluorinated polymer such as PTFE. The outer tubular layer comprises at least three longitudinally spaced, connected tubular sections. The sections are of successively increasing flexibility from the proximal toward the distal catheter end. Also, manufacturing methods are disclosed pertaining to increasing the flexibility of a section of the catheter and joining together in abutting relation a pair of dissimilar catheter reinforcement members.

14 Claims, 1 Drawing Sheet

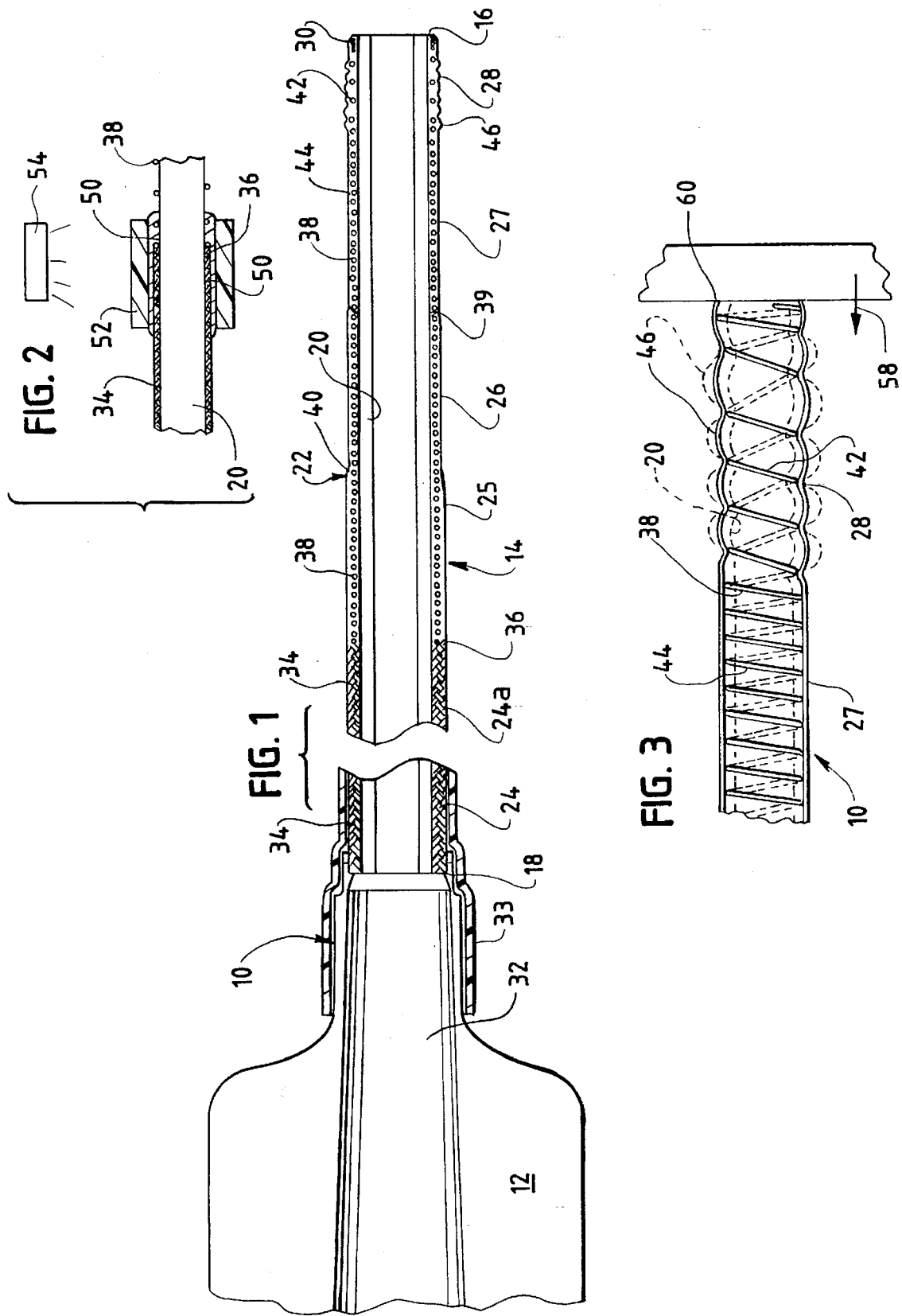

INTRAVASCULAR CATHETER

BACKGROUND OF THE INVENTION

The invention relates to an intravascular catheter which finds particular advantage in the form of a microcatheter, which is capable of penetration deeply into the branching small arteries of the heart, the brain, the liver, or other organs of the body for the application of chemotherapy or x-ray visualization of the blood vessel structure.

Brain catheters are also used for the infusion of embolic coils in aneurysms and infusion of embolic agents in arteriovenous malformations and fistulas (vessel ruptures). An example of an embolic agent or sealing agent is cyanoacrylate which embolizes or seals the required vessel. This is usually done only in the smaller branch arteries, so that a catheter used to provide such materials must have a highly flexible tip coupled with good pushability, all in conjunction with a small outside diameter. Typically, such microcatheters may have a width of no more than about 0.05 inch, or no more than substantially three French size.

In the prior art, efforts have been made to provide thin catheters which have distal ends that are more flexible than a proximal portion of the catheter. For example, Engelson U.S. Pat. No. 4,739,768 and its reexamination certificate disclose such a catheter. Sepetka U.S. Pat. No. 4,955,862 discloses a catheter having a thinner distal end which carries a helical reinforcing spring. See also Castaneda et al. U.S. Pat. No. 5,279,596.

By this invention, an intravascular catheter which is preferably of French three size or less is provided, which catheter is particularly capable of advancement into small arteries, having a stepwise gradient of increasing flexibility along the catheter extending from a proximal portion toward the distal end. The catheter is capable of advancement and deep penetration into brain arteries for example, so that a therapeutic agent may be delivered to a precise location deep inside the brain, which location would be inaccessible to many other catheters.

DESCRIPTION OF THE INVENTION

In accordance with this invention, a catheter is provided for insertion into arteries and particularly the brain arteries. The catheter comprises a flexible tube having an outer diameter of typically no more than about 0.05 inch. The flexible tube defines proximal and distal ends plus outer and inner tubular layers. The inner tubular layer surrounds a catheter lumen and comprises a chemically inert, fluorinated polymer. The outer tubular layer comprises at least three longitudinally spaced, tubular sections joined at their ends, the sections being of successively increasing flexibility from the proximal to the distal ends.

Thus, the catheter is capable of conveying chemically active therapeutic materials through a chemically inert, fluorinated polymer inner surface. Also, the catheter is capable of exhibiting successively increasing flexibility to maximize the combined characteristics of pushability of the catheter and penetrability of the distal catheter end into tiny, convoluted arteries.

Also, it is preferred for a hydrophilic friction reducing agent of conventional type to be carried on the exterior of the catheter. Additionally, the proximal end of the catheter may carry a hub which has a central bore that tapers outwardly from the distal to the proximal end of the hub.

In another aspect of this invention, an intravascular catheter is provided which comprises a flexible, tubular wall, the wall carrying a helical coil reinforcement member embedded within the tubular wall. This coil reinforcement provides radial or hoop strength for the distal end of the catheter in order to prevent collapse of the catheter as it turns through the tortuous anatomy, without adding excessive stiffness of the catheter distal end.

The helical reinforcement member typically comprises a length of wire made of metal or plastic. By this invention, the reinforcement member comprises a first coil portion having helical coils which are of a greater pitch (or spacing from adjacent coils) than the pitch of the helical coils of a second portion of the reinforcement member. In other words, the helical reinforcement member may have a first portion where the coils are stretched out more in the longitudinal direction, having an angle to the longitudinal axis that is less than the coils in the second portion of the helical reinforcement member. Thus two different catheter sections are defined by the different character of different portions of the helical reinforcement member, to produce areas of differing flexibility.

The first portion of the helical reinforcement member is preferably positioned distally from the second portion of the helical reinforcement member. Furthermore, the reinforcement member is preferably positioned adjacent the distal end of the catheter, and is shorter than the catheter, so that a proximal catheter portion is provided which is spaced from the helical reinforcement member. It is preferred for the helical reinforcement member to be spaced particularly from a proximal end portion of the catheter, with the proximal end portion comprising typically at least half of the catheter length.

The proximal end portion of the catheter preferably comprises a tubular wall which has embedded, along most of its length, a crossing-strand tubular reinforcement member such as typical catheter braiding. This braiding may be attached at one end to the embedded helical reinforcement member with adhesive or the like.

It is also preferable for the catheter to carry, distal to the catheter proximal end portion, an integrally attached, second tubular wall portion that carries some of the embedded second coil portion of the reinforcement member and, distal to the second tubular wall portion, an integrally attached, third tubular wall portion that also carries some of the embedded second portion of the helical reinforcement member. The third tubular wall portion, integral with the second wall portion, is of less outer diameter than the second wall portion, and thus provides a more flexible catheter section than that of the second wall portion. Some of the second coil portion may also be carried by the third tubular wall portion.

Also, the catheter preferably carries, distal to the third tubular wall portion, an integrally attached, fourth tubular wall portion which is made of a tubular plastic material which is softer than the corresponding tubular plastic materials positioned proximally to the fourth tubular wall portion. The fourth tubular wall portion may preferably carry some of the embedded second coil portion of the helical reinforcement member. The fourth tubular wall portion also may have an outer diameter which is substantially of equal or less outer diameter than the third tubular wall portion.

Preferably, a fifth tubular wall portion is integrally carried by the catheter distal to the fourth tubular wall portion. The fifth tubular wall portion carries the embedded first coil portion of the helical reinforcement member described above, having the greater coil spacing and pitch. Also, the fifth tubular wall portion may comprise circumferentially-extending portions of longitudinal bending weakness positioned between helical coils of the first coil portion. Thus, in the fifth tubular wall portion the catheter exhibits an improved flexibility because of the presence of wider spaced helical coils and the circumferentially-extending wall portions of longitudinal bending weakness.

Preferably, each of the tubular wall portions which are distal to the wall portions before them are more flexible than the wall portions before them, to provide a catheter of graduated flexibility, increasing in flexibility toward the distal end of the catheter, with the possible exception of the distal catheter tip. There, the coil reinforcement may be wound at a very tight pitch on the distal catheter end in order to provide a radiopaque distal marker for the catheter.

The portions of longitudinal bending weakness described above may be prepared by the following method of increasing the flexibility of at least a section of an intravascular catheter. The catheter defines a tubular plastic wall, at least a portion of which carries a helical reinforcement member which is embedded within the tubular wall with coils of the helical reinforcement member in the portion being spaced from each other. The method comprises the step of longitudinally compressing at least the portion of the tubular wall described above to cause the tubular wall portions between the spaced helical coils to stretch and bow radially inwardly or outwardly, to form the circumferentially extending portions of longitudinal bending weakness. Thereafter, one removes the catheter from the condition of longitudinal compressing, with the material of the catheter walls being weakened to exhibit greater flexibility by the longitudinal compression step.

Preferably, the plastic used is a thermoplastic material of a type which can cold flow to take a compression set by the compression step. For example, nylon, PET, or polyurethane comprise suitable thermoplastic materials for the process.

Typically, the portion of the catheter tubular wall which has the embedded coils and which is longitudinally compressed or crushed is a relatively short section of the catheter, less than a quarter of the length thereof, and which is positioned adjacent the distal end of the catheter. In this circumstance, just that portion of the catheter may be longitudinally compressed or crushed, the majority of the catheter being excluded from such a longitudinal compression step.

Such a compression step can provide the section which is so processed with a unique flexibility and softness, which is particularly useful adjacent the catheter distal tip.

Further in accordance with this invention, a method of catheter component manufacture is provided which comprises the joining together of a pair of tubular, strand-type, catheter reinforcement members in end-to-end relation prior to embedding the joined reinforcement members into a tubular plastic catheter wall. Such reinforcement members may, for example, comprise a woven or braided tubular catheter reinforcement of conventional type, joined at an end to the end of a helical wire, both of which are intended to be embedded into the catheter wall.

The method comprises joining ends of the reinforcement members together in such an end-to-end relation; placing a curable adhesive (including solder as a candidate) on the joined ends; covering the joined ends with a snug, non-adherent sleeve; and curing the adhesive. Typically, the sleeve is removed after the process is over, but it may remain as part of the catheter if that is desired.

The adhesive may be of an ultraviolet curable type, with ultraviolet radiation being applied to cure the adhesive and join the pair of reinforcement members together in an adhesive bond that is formed underneath the sleeve. The sleeve in this circumstance will be substantially transparent to ultraviolet radiation. Such sleeves may be made out of fluorinated plastics which are both non-adherent and ultraviolet permeable, for example FEP plastic or the like.

The catheter of this invention also preferably comprises a chemically inert, fluorinated polymer tube such as PTFE surrounding its lumen, or at least one of its lumens if it is a multi-lumen catheter. Thus, x-ray contrast fluid or reactive therapeutic materials can pass through the catheter in contact with a chemically inert surface provided by the fluorinated polymer to inner, narrow portions of the vascular system of the patient as may be needed.

DESCRIPTION OF THE DRAWINGS

FIG. 1 is an enlarged longitudinal sectional view of the proximal and distal end portions of the catheter of this invention;

FIG. 2 is an enlarged longitudinal sectional view of a portion of the catheter of FIG. 1 showing it in an intermediate stage of manufacture; and FIG. 3 is an enlarged longitudinal sectional view of a modified proximal end of the catheter of FIG. 1, showing the catheter being processed in accordance with this invention for improved flexibility of the distal end.

DESCRIPTION OF SPECIFIC EMBODIMENTS

Referring to the drawings, a microcatheter 10 for penetration through the arteries into the brain is disclosed. Catheter 10 carries a hub 12 which defines its proximal end, and a flexible tubular wall 14 extending distally from hub 12 to define the catheter body. Typically, catheter 10 may have a length of about 75–175 cm, specifically 155 cm. The outer diameter of the catheter at its distal end 16, may be 2.5 French, (or less) while the outer diameter near the proximal end of catheter body 14 may be 3.0 French.

Catheter body 14 comprises an inner, lumen defining tube of polytetrafluoroethylene (PTFE) 20 having a wall thickness of about 0.002 inch, as is conventional for certain cardiovascular catheters. Outside of the PTFE tube 20 there is positioned the thicker, outer catheter portion 22 comprising a tubular plastic material, typically having a tubular reinforcement embedded therein. This outer tubular layer comprises a plurality of connected, longitudinally spaced tubular sections 24–30. Tubular sections 24–28, in particular, are sections of successively increasing flexibility from the proximal end of the catheter tube 18 to the distal end 16, with the possible exception of optional, ringlike tubular section 30 at the distal tip 16.

Catheter hub 12 may be of conventional design, defining a central bore 32 that tapers outwardly from the distal end of the hub adjacent catheter body end 18, to the opposed, proximal hub end. The smooth, gradual taper of bore 32 can prevent blockage of embolic materials which may be passed to the brain or liver through the catheter. Hub 12 may be made of nylon or polysulfone, for example, and may be attached in conventional manner to catheter body 14, being reinforced by a tubular plastic strain relief 33.

A substantial distal portion of the catheter may have an exterior coating of a known hydrophilic friction reducing agent for catheters.

A proximal end portion 24 of the tubular catheter body of wall 14 comprises the tubular wall made of a thermoplastic with a conventional, metallic, tubular, fibrous braid for catheters 34 being embedded therein. The first or proximal tubular portion 24 may be about 100 cm in length, and may comprise a nylon material having a Shore D durometer of about 75 (Vestamid 75D).

The added integral tubular portion 24a may be identical to portion 24 and bonded thereto, but with the tubular wall being made of the softer Vestamid 64D nylon, having a Shore D durometer of 64, having a length of about 25 cm., and containing a portion of the same braid 34.

Distal of the proximal catheter end portion that carries the braided reinforcement 34 is a second tubular wall portion 25 which is bonded to catheter wall section 24a in area 36. This second catheter tubular wall portion 25 also carries, embedded therein, a proximal portion of helical reinforcement member 38, while the braided tubular member 34 terminates, but is connected to helical member 38. Also, second tubular wall portion 25 may be made of a polyurethane material, for example a polyurethane having a Shore D durometer of about 65 (Pellethane 65D).

Second tubular wall portion 25 connects at its distal end to a third tubular Wall portion 26 which also carries some of the same helical reinforcement 38. Third tubular wall portion 26 is of reduced diameter compared with second tubular wall portion 25 and integral therewith, being separated by an annular taper portion 40 at the integral connection between the two wall portions 25, 26. Taper portion 40 may be about 1 cm in length.

Wall portion 26 may be made of the same material as wall portion 25, with the combined length of the two tubular wall portions 25, 26 being about 15 cm.

Distal to tubular wall portion 26, a fourth tubular wall portion 27 is integrally attached to portion 26, with wall portion 27 also incorporating and embedding a portion of helical reinforcement 38. Tubular wall portion 27 may be made of a different, softer polyurethane thermoplastic material having a Shore A durometer of about 80 (Pellethane 80A), and optionally with a wall portion of reduced diameter compared with third wall portion 26, and a length of about 11 cm. A taper 39 of about 1 cm is used here too.

Fifth tubular wall portion 28 is integral with the distal end of fourth tubular portion 27, being made of the same wall-forming thermoplastic material as portion 27. However, as shown in FIGS. 1 and 3, the individual coils 42 of the helical reinforcement member 38 are more widely spaced from each other in fifth wall portion 28 than are the corresponding coils 44 in their spacing in catheter wall portions 25–27. Specifically, the spacing between the coils 42 in wall portion 28 may be about 0.026 inch, while the spacing of the corresponding individual coils 44 in catheter wall portion 27 may be about 0.014 inch. Fifth wall portion 28 is about 3.8 cm long.

By a process which is described below, fifth tubular wall portion 28 comprises circumferentially extending portions of longitudinal bending weakness 46 of the plastic material between the respective coils 42 of the helical reinforcement 38. These spaced coils 42 comprise the first portion of the helical reinforcement member 38, having a greater pitch and more spacing than the corresponding coils 44 of the second helical portion of reinforcement member 38.

A tip member 30 or sixth tubular wall portion may be provided to the catheter at distal tip 16, where the coils of helical reinforcement member 38 are once again close together or even in contact. This provides good x-ray visualization to the tip when coil 38 is made of metal, and also good hoop strength. This portion is only about 0.1 cm long.

Referring to FIG. 2, a method is disclosed for joining together a pair of tubular, strand-type catheter reinforcement members in end-to-relation, specifically braiding 34 and helical member 38, which may be joined together at junction point 36. This is typically accomplished prior to embedding the joined reinforcement members into a tubular plastic catheter wall. The reinforcement members may be threaded over the inner lumen-defining tube 20 if desired for support.

The respective catheter reinforcement members 34, 38 are brought together into abutting, end-to-end relation as shown in FIGS. 1 and 2.

One places a curable adhesive 50 on the joined ends. Then, one covers the joined ends and the curable adhesive with a snug, non-adherent sleeve 52 which may typically be made of FEP, centering the sleeve on junction 36 if desired. Specifically, an ultraviolet-curable adhesive may be used in this circumstance, with a source of ultraviolet radiation 54 irradiating all outer sides of the arrangement. Ultraviolet radiation passes through the FEP sleeve to cure the mass of adhesive 50 while encasing junction 36. Alternatively, a molten silver solder may be applied as the adhesive, the curing taking place by solidification on cooling.

Prior to the cure, the application of sleeve 52 forces the adhesive into the spaces between the respective strands of tubular reinforcements 34, 38 and causes the creation of a smooth, cylindrical outer coating of adhesive which is little or no thicker than the respective reinforcement members 34, 38, so that the resulting product can be smooth to the touch and not significantly wider than the remainder of the final catheter. Following this, sleeve 52 may be removed, it being substantially non-adherent to the adhesive 50.

The 360° radiation cure is either provided by rotating the assembly shown in FIG. 2 or by providing a series of radiation sources 54 placed peripherally about junction 36 of the catheter, for complete, 360° irradiation of the adhesive 50.

Following this, the joined reinforcement members 34, 38, threaded on PTFE tube 20 if desired, may be placed in an appropriate extrusion die, so that outer catheter wall 22 is extruded in one or more application steps over the catheter component shown in FIG. 2. Thus, the two reinforcement members 34, 38 are firmly joined together at a junction which is essentially invisible from the exterior without careful investigation.

One will note that in the embodiment shown, adhesive 50 is at the location of the future bond between different plastics found at junction 36. Tubular wall 24a comprises nylon, while tubular wall 25 comprises polyurethane. Added strength to the catheter is provided by the adhesive 50 at this point.

Referring now to FIG. 3, a method is provided for increasing the flexibility of the distal tip portion of catheter 10. The specific design of catheter tip shown in FIG. 3 omits the distal end portion 30 of the catheter, showing an alternate embodiment.

By this invention, the coils 42 of helical reinforcement 38 are more widely spaced than other coils 44 in the same helical reinforcement. At least the section of the catheter having the more widely spaced helical coils in the catheter wall is longitudinally compressed as shown by the use of a compression plate 56, or by grasping spaced portions of the catheter and compressing them together. Catheter distal end 60 is moved in the direction of arrow 58 to longitudinally compress catheter 10. By this inventive step, the portions of longitudinal bending weakness 46 are created by forcing the catheter wall of section 28 to bow outwardly, both the outer, thermoplastic portion, and also the PTFE inner liner 20 in that section. The effect of this longitudinal compression is to weaken the bending resistance of the respective wall portions 46, providing further softness and compliance to the catheter in section 28 above and beyond the softness and compliance of the adjacent Catheter sections, for example catheter portion 27. This effect is magnified by the fact that coils 42 of the helical support member 38 are more widely spaced in tubular portion 28 than elsewhere.

It is also possible for the portions 46 to bow inwardly under certain circumstances to achieve the same effect. The PTFE inner layer participates in the bending weakening that results therefrom.

Then, the catheter is removed from the condition of longitudinal compressing, and is ready for further processing or for use.

Specifically, the outer tubular wall 22 of the catheter may have a thickness of 0.004 to 0.005 inch in sections 24, 24a and 25, and 0.0025 to 0.005 in sections 26–30.

The above has been offered for illustrative purposes only, and is not intended to limit the scope of the invention of this application, which is as defined in the claims below.

That which is claimed:

1. An intravascular catheter which comprises a flexible tubular wall, said wall carrying a helical reinforcement member embedded within said tubular wall, said helical reinforcement member comprising a helical first portion having helical coils of greater pitch than the pitch of helical coils of a second helical portion of said reinforcement member, said helical reinforcement member being connected to but spaced from a proximal end portion of said catheter, said proximal end portion comprising at least half of the catheter length, said proximal end portion comprising a portion of said tubular wall embedded along most of its length with a second reinforcement member, said second reinforcement member comprising a crossing-strand, tubular reinforcement; said catheter carrying, distal to said proximal end portion, an integrally attached, second tubular wall portion comprising part of said tubular wall, said second tubular wall portion carrying some of said embedded second helical portion of said reinforcement member, and, distal to said second tubular wall portion, an integrally attached, third tubular wall portion comprising part of said tubular wall, said third tubular wall portion carrying some of said embedded, second helical portion of said helical reinforcement member, said third wall portion being of less outer diameter than said second wall portion; said catheter carrying, distal to said third tubular wall portion, an integrally attached, fourth tubular wall portion comprising part of said tubular wall, said fourth tubular wall portion being made of a tubular plastic material which is softer than the corresponding tubular plastic materials positioned proximal to said fourth tubular wall portion.

2. The catheter of claim 1 in which said first helical portion is positioned distally from said second helical portion of the helical reinforcement member, said reinforcement member being positioned adjacent the distal end of said catheter.

3. The catheter of claim 2 in which a fifth tubular wall portion comprising part of said tubular wall is integrally carried distal to said fourth tubular wall portion, said fifth wall portion carrying said embedded first helical portion of the helical reinforcement member.

4. The catheter of claim 3 in which said fifth tubular wall portion comprises circumferentially-extending portions of longitudinal bending weakness between helical coils of said first helical portion.

5. The catheter of claim 1 in which said tubular wall comprises circumferentially-extending portions of longitudinal bending weakness positioned between helical coils of said first helical portion.

6. The catheter of claim 5 in which said first helical portion is positioned distally from said second helical portion of the helical reinforcement member.

7. The catheter of claim 2 in which said fourth tubular wall portion carries some of said embedded second helical portion of said helical reinforcement member.

8. The catheter of claim 1 having a distal tip, and having helical coils of said reinforcement member, some of said coils occupying said distal tip at a pitch that is less than the pitch of the remaining coils.

9. A catheter for insertion into blood vessels, said catheter comprising a flexible tube having an outer diameter of no more than about 0.05 inch, said flexible tube defining proximal and distal ends and having outer and inner tubular layers, said inner tubular layer surrounding a catheter lumen and comprising a chemically inert, fluorinated polymer; said flexible tube carrying a helical reinforcement member embedded within said tube adjacent a distal end of said catheter, said helical reinforcement member being spaced from a proximal end portion of said catheter, said proximal end portion comprising at least about half of the catheter length, said proximal end portion comprising said tube embedded along most of its length with a crossing-strand, tubular reinforcement member; said proximal end portion defining a softer, distally positioned portion that comprises a softer plastic material than other portions of said proximal end portion; said catheter having, adjacent to and distal of said proximal end portion, an integrally attached, second tubular wall portion comprising part of said flexible tube and which carries some of said embedded helical reinforcement member and, distal to said second tubular wall portion, an integrally attached third tubular wall portion comprising part of said flexible tube and which carries some of said embedded, helical reinforcement member, said catheter having, distal to said third tubular wall portion, an integrally attached, fourth tubular wall portion comprising part of said flexible tube and comprising a tubular plastic material which is softer than the corresponding tubular plastic materials positioned proximal to said fourth tubular wall portion, said fourth tubular wall portion carrying some of said embedded helical reinforcement member, said proximal end portion having a larger outer diameter then said fourth portion.

10. The catheter of claim 9 having a distal tip, and having helical coils of said reinforcement member embedded in said distal tip and being closer together than remaining coils of said reinforcement member.

11. The catheter of claim 10 in which sections of the outer tubular layer are of successively increasing flexibility from the proximal end toward the distal end.

12. The catheter of claim 11 in which said catheter also has a fifth tubular wall portion distal to said fourth tubular wall portion and proximal of said distal tip, said fifth wall portion comprising part of said flexible tube and carrying some of said embedded, helical reinforcement member, said fifth tubular wall portion comprising circumferentially-extending portions of longitudinal bending weakness between helical coils of said reinforcement member.

13. The catheter of claim 12 in which the second and third tubular wall portions comprise the same plastic material.

14. The catheter of claim 10 in which a hydrophilic friction reducing agent is coated on the exterior of said tube.

* * * * *